US009683076B2

(12) United States Patent
Begotti

(10) Patent No.: US 9,683,076 B2
(45) Date of Patent: Jun. 20, 2017

(54) PROCESSES FOR RECOVERING AND PURIFYING POLYHYDROXYALKANOATES FROM CELL CULTURES

(71) Applicant: BIO-ON S.p.A., San Giorgio di Piano (IT)

(72) Inventor: Simone Begotti, San Giorgio di Piano (IT)

(73) Assignee: BIO-ON S.P.A., San Giorgio di Piano (IT)

( * ) Notice: Subject to any disclaimer, the term of this patent is extended or adjusted under 35 U.S.C. 154(b) by 0 days.

(21) Appl. No.: 14/908,456

(22) PCT Filed: Jul. 28, 2014

(86) PCT No.: PCT/IB2014/063475
§ 371 (c)(1),
(2) Date: Jan. 28, 2016

(87) PCT Pub. No.: WO2015/015395
PCT Pub. Date: Feb. 5, 2015

(65) Prior Publication Data
US 2016/0168319 A1  Jun. 16, 2016

(30) Foreign Application Priority Data
Jul. 30, 2013 (IT) .............................. MI2013A1276

(51) Int. Cl.
| | | |
|---|---|---|
| *C08G 64/00* | (2006.01) | |
| *C08G 63/90* | (2006.01) | |
| *C12P 7/62* | (2006.01) | |
| *C08G 63/06* | (2006.01) | |
| *C08G 63/89* | (2006.01) | |
| C08G 63/02 | (2006.01) | |

(52) U.S. Cl.
CPC ............. *C08G 63/90* (2013.01); *C08G 63/06* (2013.01); *C08G 63/89* (2013.01); *C12P 7/625* (2013.01)

(58) Field of Classification Search
CPC ...................................................... C07C 29/60
USPC ................... 528/361; 435/135; 436/129, 135
See application file for complete search history.

(56) References Cited

U.S. PATENT DOCUMENTS

| | | | |
|---|---|---|---|
| 5,437,986 A | 8/1995 | Alroy et al. | |
| 7,314,740 B2 | 1/2008 | Miyamoto et al. | |
| 7,393,668 B2 | 7/2008 | Yanagita et al. | |
| 7,435,567 B2 * | 10/2008 | Osakada ............... | C12M 47/06 435/135 |
| 7,514,525 B2 | 4/2009 | Yu | |
| 2005/0196827 A1 | 9/2005 | Osakada et al. | |
| 2008/0220505 A1 | 9/2008 | Yu | |
| 2012/0252081 A1 | 10/2012 | Yu | |

FOREIGN PATENT DOCUMENTS

| | | |
|---|---|---|
| EP | 1739182 A1 | 3/2007 |
| WO | WO-2011/045625 A1 | 4/2011 |

OTHER PUBLICATIONS

Stuart M. Bailey, et al., "Separation of soluble protein from inclusion bodies in *Escherichia coli* lysate using crossflow microfiltration", 2000, Journal of Membrane Science, vol. 166, pp. 137-146.
Patrick Christian Furrer, "Medium-chain-length poly([R]-3-hydroxyalkanoates): from biosynthesis towards medical applications", 2008, Diss. ETH No. 17654, pp. 1-141, XP055142902.
MS Ghatnekar, et al., "Production and recovery of poly-3-hydroxybutyrate from *Methylobacterium* sp V49", 2002, Journal of Chemical Technology and Biotechnology, vol. 77, pp. 444-448, XPOD1577445.
B. Kunasundari, et al., "Isolation and recovery of microbial polyhydroxyalkanoates", 2011, eXPRESS Polymer Letters, Vo. 5, No. 7, pp. 620-634, XP055110780.
Martin Koller, et al., "Strategies for recovery and purification of poly[(R)-3-hydroxyalkanoates] (PHA) biopolyesters from surrounding biomass" 2013, Engineering in Life Sciences, pp. 549-562, XP055110776.
International Search Report PCT/ISA/210 for International Application No. PCT/IB2014/063475 Dated Oct. 7, 2014.
Written Opinion of the International Searching Authority PCT/ISA/237 for International Application No. PCT/IB2014/063475 Dated Oct. 7, 2014.

* cited by examiner

*Primary Examiner* — Terressa Boykin
(74) *Attorney, Agent, or Firm* — MH2 Technology Law Group, LLP

(57) ABSTRACT

A process for recovering and purifying polyhydroxyalkanoates from a cell culture may include: (a) acidifying the culture to obtain a pH value less than or equal to 6, and submitting the culture to a cell fractionation treatment using high-pressure homogenization at a temperature greater than or equal to 10° C. and less than or equal to 80° C. to obtain a suspension; (b) basifying the suspension to obtain a pH value greater than or equal to 8; (c) diluting the suspension and submitting the diluted PHA suspension to tangential filtration to obtain a concentrated suspension as retentate and an aqueous phase as permeate; (d) submitting the concentrated suspension to bleaching; (e) diluting the suspension after the bleaching and submitting the diluted bleached suspension to tangential filtration to obtain a concentrated bleached suspension as retentate and an aqueous phase as permeate; and/or (f) submitting the concentrated bleached suspension to drying.

20 Claims, No Drawings

PROCESSES FOR RECOVERING AND PURIFYING POLYHYDROXYALKANOATES FROM CELL CULTURES

CROSS-REFERENCE TO RELATED APPLICATION(S)

This application is a national stage entry from International Application No. PCT/IB2014/063475, filed on Jul. 28, 2014, in the Receiving Office of the International Bureau of the World Intellectual Property Organization ("WIPO") and published as International Publication No. WO 2015/015395 A1, which claims priority from Italian Patent Application No. MI2013A001276, filed on Jul. 30, 2013, in the Italian Patent and Trademark Office, the entire contents of both of which are incorporated herein by reference.

The present invention concerns a process for recovering and purifying polyhydroxyalkanoates from a cell culture.

Polyhydroxyalkanoates (PHA) are hydroxyalkanoate homopolymers or copolymers, such as 3-hydroxybutyrate (3HB), 3-hydroxyvalerate (3HV), 4-hydroxyvalerate (4HV) and 3-hydroxyhexanoate (3HH). They are synthesized and accumulated by various microorganisms, in particular bacteria, as carbon and energy reserve for cell metabolism. PHA can be produced by fermentation of suitable strains of bacteria on an organic substrate, usually based on carbohydrates, alcohols and organic acids. Biopolyesters are synthesized and stored by the cells from which they must then be extracted so as to obtain the polymer material with a sufficient degree of purity.

With respect to the synthetic polymers and to other biopolymers obtained from renewable sources (for example polylactic acid (PLA)), PHA have numerous advantages, in particular in terms of biodegradability, recyclability and hydrophobicity, which make such products particularly promising as biodegradable substitutes of polymers of petrochemical origin.

The process for producing PHA, after the fermentation step in which the bacterial cells synthesize the polymer and accumulate it inside themselves, requires a step of removing the PHA from the cells wherein the cell walls are destroyed and separated from the PHA, and a step of purifying and bleaching the PHA.

A method for removing PHA from cells that produced it includes the use of organic solvents that are capable of solubilising the polymer, as described for example in patent application EP 1,739,182 A1. Such method has numerous drawbacks, in particular, due to high viscosity of PHA solutions which, in order to be processed, must be diluted with huge amounts of solvent, with evident problems in terms of its recovery and of process costs. Moreover, the PHA thus recovered must then be separated from the organic solvent, for example by precipitation by adding another solvent in which the PHA is poorly soluble. This makes the process with solvents extremely costly and problematic as far as the environment is concerned.

U.S. Pat. No. 7,314,740 B2 describes a process for producing PHA which comprises carrying out a step for breaking the cell membranes which contain the PHA by adding an alkaline substance, for example a strong base, so as to obtain a pH value from 9 to 13.5 and simultaneously a mechanical action on the suspension carried out for example through an emulsifying device or a high pressure homogenizer. The polymer is then separated by centrifugation.

U.S. Pat. No. 7,393,668 B2 concerns a method for recovering PHA from cells that produced it by: (a) adding an alkaline product under stirring and mechanical action for breaking the cell membranes with solubilization of the biological material, and subsequent separation of the PHA; and (b) treatment of the PHA thus obtained with an enzyme and/or a surfactant for solubilizing impurities contained in the PHA, and subsequent washing of the PHA with a hydrophilic solvent and/or water. In particular, to avoid a reduction in the PHA molecular weight, the mechanical breaking step of the cell membranes is obtained before adding the alkaline product, since it is believed that the mechanical action carried out after the alkalization step can lead to a substantial and undesired reduction in the polymer molecular weight. The cell breaking can be obtained by means of a high pressure homogenizer, an ultrasound device, an emulsifying device, a mill etc.

U.S. Pat. No. 7,514,525 describes a method for recovering, purifying and isolating PHA from a cell mass that contains it, comprising: (a) solubilising the cell mass different from PHA in an acidic solution, forming a suspension of partially crystallised PHA granules; (b) adjusting the pH of the suspension to a value from 7 to 11 and separating the solid PHA from the dissolved cell mass; (c) re-suspending the solid PHA in a bleaching solution; (d) drying the solid PHA thus obtained. The solubilisation according to step (a) is carried out at high temperature and for long periods of time, in particular at 80°–130° C., preferably 100°-110° C., for a time from 30 minutes to 4 hours, preferably 2 hours. The separation of the solid PHA from the dissolved cell mass is obtained by prolonged high speed centrifugation (4000 g for 20 minutes).

The present invention has mainly the purpose of providing a process for recovering and purifying PHA from a cell mass containing the same that can be carried out continuously, i.e. without steps in batches like for example centrifugation steps for separating the PHA from a suspension, which are generally complex to carry out in great volumes, require the use of costly machinery and unavoidably reduce the process productivity. Another aim of the present invention is that of carrying out the process without using organic solvents, which, as illustrated above, in addition to leading to considerable difficulties in performing the process on a large scale, are undesirable from an ecological point of view. A further aim is that of obtaining the PHA in a form that is as pure as possible without causing a reduction in the molecular weight, which would have unavoidable consequences on the mechanical performance of the polymer material.

The Applicant has now found that these and other purposes, which will be illustrated more in detail in the rest of the description, can be achieved with a process as defined hereinbelow and in the attached claims.

In a first aspect, the present invention thus concerns a process for recovering and purifying polyhydroxyalkanoates (PHA) from a cell culture, which comprises:

(a) acidifying the cell culture so as to obtain a pH value equal to or lower than 6, and submitting said cell culture to a cell fractionation treatment by means of high pressure homogenization at a temperature from 10° C. to 80° C., so as to obtain a PHA suspension;

(b) basifying the PHA suspension thus obtained so as to obtain a pH value equal to or higher than 8;

(c) diluting the PHA suspension and submitting it to tangential filtration so as to obtain a concentrated PHA suspension as retentate and an aqueous phase as permeate;

(d) submitting the PHA suspension to a bleaching step;

(e) diluting the PHA suspension after the bleaching step and submitting it to tangential filtration so as to obtain a concentrated bleached PHA suspension as retentate and an aqueous phase as permeate;

(f) submitting the concentrated bleached PHA suspension to drying.

The starting cell culture in general comes from a fermentation process that is carried out on a nutritional organic substrate by strains of bacteria that are capable of producing PHA. Such strains of bacteria can be selected for example from the following genera: *Cupriavidus, Azotobacter, Alcaligenes, Aeromonas, Nocardia, Ralstonia, Pseudomonas, Alcaligenes, Methylobacterium, Bacillus*. Particularly preferred are the genera *Ralstonia, Cuprividus* and *Methylobacterium*, and more specifically the species *Ralstonia eutropha, Cupriavidus necator* and *Methylobacterium rhodesianum*.

The nutritional substrate can be any type of substrate that can be metabolised by the bacteria cells to produce PHA, which may be selected from juices, molasses or pulps obtained, for example, by processing vegetable products, such as fruit, beet sugar, sugar cane, oily seeds, and the like. Such substrates, in addition to carbohydrates and proteins, in general contain growth factors of various nature, compounds containing nitrogen and/or phosphorus and other elements useful for cell growth.

At the end of the fermentation step, the cell culture possibly may be subjected to a preliminary concentration step, with the purpose of reducing the volumes to be treated in the subsequent steps. Preferably, the preliminary concentration step leads to obtaining a cell concentration from 20 to 800 g/L, more preferably from 40 to 500 g/L. Such a concentration step can be advantageously carried out by tangential filtration, according to methods that are analogous to those subsequently described in relation to step (c).

According to step (a), the cell culture is acidified so as to obtain a pH value equal to or lower than 6, preferably equal to or lower than 5. The acidification is in general obtained by adding an acid at room temperature, in particular an aqueous solution of an inorganic or organic acid, which is selected for example from: sulphuric acid, hydrochloric acid, phosphoric acid, nitric acid, acetic acid, citric acid, or mixtures thereof.

The cell culture thus acidified is then subjected to a cell fractionation treatment that requires the use of a high pressure homogenizer. Such process may be performed continuously through the passage of the liquid from a high pressure zone to a low pressure zone, so as to submit the cells to a mechanical shock such as to fragment the cell membranes and free up the content thereof. In general, in accordance with techniques that are well known to a person skilled in the art, the homogenizer comprises a piston volumetric pump and a valve having an adjustable geometry, in which a dynamic pressure is generated in continuous flow conditions.

Preferably, in the high pressure zone, a pressure is applied from 500 bar to 2000 bar, more preferably from 500 bar to 1500. In general the homogenization process requires from 1 to 5 passages inside the device, and the number of passages required in order to obtain a sufficient degree of cell fractionation decreases as the maximum applied pressure increases.

During the homogenization process, mechanical action exerted on the cell suspension causes a temperature increase, which is in any case maintained inside the interval from 10° C. to 80° C., preferably from 20° C. to 50° C., in order to avoid possible degradations of the PHA with a consequent decrease in the average molecular weight.

After the homogenization step, the PHA suspension is basified so as to obtain a pH value that is equal to or higher than 8, preferably equal to or higher than 9. The basifying step may be preferably carried out by adding a strong base, for example a strong inorganic base solution, such as potassium hydroxide, sodium hydroxide or mixtures thereof.

In one preferred embodiment, the PHA suspension thus basified is treated with at least one surfactant at a temperature from 10° C. to 80° C., preferably from 20° C. to 50° C.

The surfactant is preferably added in low quantities, for example from 0.5 to 10 g/L, and mainly has the function of promoting elimination from the PHA of the residue deriving from the cell membrane breaking.

As surfactants, anionic, cationic, or non-ionic surfactants are preferably used. Such surfactants are preferably selected from those having low environmental impact, so as to avoid disposal problems. Examples of anionic surfactants are: alkyl or alkenyl sulphates, alkyl or alkenyl benzenesulfonates, alkyl or alkenyl ether sulphates, alkyl or alkenyl carboxylates, alkyl or alkenyl ether carboxylates, and the like. Particularly preferred are alkyl sulphates $C_{10}$-$C_{18}$.

As cationic surfactants it is possible to use for example alkyltrimethylammonium or dialkyldimethylammonium salts.

As non-ionic surfactants, it is possible to use: polyoxyalkylene (preferably polyoxyethylene) alkyl or alkenyl ethers, polyoxyalkylene (preferably polyoxyethylene) alkyl or alkenyl phenylethers, polyoxyethylene/polyoxypropylene copolymers, and the like.

After the treatment according to step (b), the PHA suspension is diluted, generally with water, so as to obtain a solid concentration that is preferably from 10 to 500 g/L, more preferably from 25 to 100 g/L, and then subjected to tangential filtration so as to obtain a concentrated PHA suspension as retentate and an aqueous phase as permeate. The tangential filtration can be carried out according to known methods by causing the suspension to pass in a continuous manner through at least one tangential flow filter, in which there is at least one ceramic or polymeric membrane, having a mean pore dimension preferably from 0.05 µm to 10 µm, more preferably from 0.2 µm to 5 µm. Such method allows to separate the retentate from the permeate by continuously passing the entering suspension through channels, preferably tubular channels, defined by the membrane substantially having a cylindrical development. Preferably, the PHA suspension to be submitted to tangential filtration is fed through said at least one tangential flow filter with a pressure that may preferably vary from 1 to 10 bar, more preferably from 2 to 6 bar.

The mean dimension of the PHA suspended particles is in general comprised from 0.3 µm to 2 µm, preferably from 0.5 µm to 1.5 µm. The presence of particles with dimensions that are so small may lead to a rapid obstruction of the tangential filter due to so-called "fouling" of the surfaces through which the suspension flows, which leads to alteration and reduction of permeability of the filtering surface. To reduce such phenomenon, it is preferable to keep a flow rate through the tangential filter comprised from 2 to 10 m/sec, more preferably from 3 to 8 m/sec.

The concentrated PHA suspension obtained as retentate from the tangential filtration step (c) thus undergoes a bleaching step, which may be obtained, for example, by adding an oxidizing agent, in particular an aqueous solution of a hypochlorite (for example sodium hypochlorite) or, preferably, of hydrogen peroxide. A particularly preferred solution is hydrogen peroxide with a concentration from 10% to 35% by weight. Preferably, the bleaching step is carried out at a temperature from 10° C. to 60° C.

After the treatment according to step (d), the bleached PHA suspension is diluted, in general with water, so as to obtain a solid concentration preferably from 10 g/L to 100 g/L, and is then subjected to tangential filtration so as to obtain a concentrated bleached PHA suspension as retentate and an aqueous phase as permeate. Such tangential filtration step can be carried out in a way analogous to the aforementioned step (c).

The concentrated bleached PHA suspension then undergoes drying, according to conventional methods, in particular through a hot air flow. For such purpose it is possible to use a spray dryer, a fluid bed dryer and the like.

In a preferred embodiment, the concentrated bleached PHA suspension obtained from step (e) is further concentrated by means of orthogonal filtration and is then fed to the drying step (f). In such a way the time necessary to obtain drying and the relative energy consumption are reduced. The orthogonal filtration can become necessary in the case in which it is desired to obtain a suspension even more concentrated with respect to the limits obtainable by tangential filtration.

The possible orthogonal filtration of the PHA suspension can be carried out by a drum filter, a rotary filter or a candle filter. Since the particles have small dimensions, in order to avoid a premature clogging of the filter with consequent stopping of the permeation of the aqueous phase (impermeabilization), it is preferable to add at least one flocculating agent to the concentrated bleached PHA suspension, preferably at least one non-polymeric flocculating agent, so as to prevent contamination of the final PHA. Preferably, said at least one flocculating agent is selected from inorganic products such as: calcium oxide, aluminium sulphate, phosphoric acid, and mixtures thereof.

As regards the PHA to which the process in accordance with the present invention may be applied, these are in general polymers containing repeating units of formula:

$$-O-CHR_1-(CH_2)_n-CO- \quad (I)$$

wherein:
$R_1$ is selected from: —H, alkyls $C_1$-$C_{12}$, cycloalkyls $C_4$-$C_{16}$, alkenyls $C_2$-$C_{12}$, possibly substituted with at least one group selected from: halogen (F, Cl, Br), —CN, —OH, —COOH, —OR, —COOR (R=alkyl $C_1$-$C_4$, benzyl);
n is an integer from 1 to 6, preferably is 1 or 2.

Preferably, $R_1$ is methyl or ethyl, and n is 1 or 2.

The PHA can be homopolymers, copolymers or terpolymers. In the case of copolymers or terpolymers, these can consist of different repeating units of formula (I), or of at least one repeating unit of formula (I) in combination with at least one repeating unit deriving from comonomers which are capable of copolymerising with hydroxyalkanoates, for example lactones or lactams. In this last case, the repeating units of formula (I) are present in an amount equal to at least 10% in moles with respect to total moles of repeating units.

Particularly preferred repeating units of formula (I) are the ones derived from: 3-hydroxybutyrate, 3-hydroxyvalerate, 3-hydroxyhexanoate, 3-hydroxyoctanoate, 3-hydroxyundec-10-enoate, 4-hydroxyvalerate.

Particularly preferred PHA are: poly-3-hydroxybutyrate (PHB), poly-3-hydroxyvalerate (PHV), poly-3-hydroxyhexanoate (PHH), poly-3-hydroxyoctanoate (PHO), poly(3-hydroxybutyrate-co-3-hydroxyvalerate) (PHBV), poly(3-hydroxybutyrate-co-3-hydroxyhexanoate) (PHBH), poly(3-hydroxybutyrate-co-4-hydroxybutyrate), poly(3-hydroxyoctanoate-co-3-hydroxyundecen-10-enoate) (PHOU), poly(3-hydroxybutyrate-co-3-hydroxyvalerate-co-4-hydroxyvalerate (PHBVV), or mixtures thereof.

The following working examples are provided purely to illustrate the present invention and must not be intended to limit the scope of protection defined by the attached claims.

EXAMPLE 1

A fermentation process was carried out by a *Ralstonia eutropha* strain on an organic molasses-based substrate deriving from processing of sugar beet, so as to obtain a cell concentration equal to 80 g/L.

The culture broth was concentrated by a tangential flow filter having a pore diameter (cut-off) equal to 1.2 μm, so as to obtain a cell concentration equal to 150 g/L.

The cell culture thus concentrated was added to a sulphuric acid solution (concentration 10% by weight), in an amount such as to obtain a pH value equal to about 4.5.

The acidified culture was then introduced into a high pressure homogenizer (maximum pressure: 1500 bar), at room temperature. The homogenization process was carried out continuously with three consecutive passages inside the homogenizer.

The PHA suspension thus obtained was then added with a sodium hydroxide solution (concentration 50% by weight), so as to obtain a pH value equal to about 10.0, and then with a sodium dodecyl sulphate aqueous solution (4 g of surfactant per liter of suspension), keeping the suspension at room temperature.

The suspension thus treated was then diluted in ratio 1:4 with water, and then subjected to filtration through a tangential flow filter with a cut-off equal to 0.8 μm, so as to obtain a solid concentration equal to 150 g/L.

The concentrated PHA suspension thus obtained was then subjected to bleaching by addition of a hydrogen peroxide solution at 30% by weight, in ratio 1:8 with respect to the volume of the suspension.

After diluting with water in ratio 1:3, the bleached suspension was subjected to a tangential filtration with a filter of the same type used after the basifying step (cut-off: 0.8 μm). The retentate contained the granules of purified PHA, whereas the permeate was used for the aforementioned dilution steps.

The retentate was subjected to drying through a spray dryer at 240° C., so as to obtain a PHA powder with a water content lower than 1% by weight.

EXAMPLE 2

The same culture broth as in Example 1 was treated as follows for recovering and purifying the PHA.

The culture broth was concentrated by a tangential flow filter having a cut-off equal to 0.4 μm, so as to obtain a cell concentration equal to 250 g/L.

The cell culture thus concentrated was added with a sulphuric acid solution (concentration 30% by weight), in an amount such as to obtain a pH value equal to about 4.5.

La acidified culture was then introduced into a high pressure homogenizer (maximum pressure: 1000 bar), at room temperature. The process of homogenization was carried out continuously with two consecutive passages inside the homogenizer.

The PHA suspension thus obtained was then added with a sodium hydroxide solution (concentration 30% by weight), so as to obtain a pH value equal to about 9.0, and then with a sodium dodecyl sulphate aqueous solution (5 g of surfactant per liter of suspension), keeping the suspension at room temperature.

The suspension thus treated was then diluted in ratio 1:3 with water, and then subjected to filtration through a tangential flow filter having a cut-off that is equal to 0.4 μm, so as to obtain a concentration of solids that is equal to 150 g/L.

The concentrated PHA suspension thus obtained was then subjected to bleaching by addition of a hydrogen peroxide solution at 30% by weight, in ratio 1:4 with respect to the volume of the suspension.

After diluting with water in ratio 1:3, the bleached suspension was subjected to tangential filtration with a filter of the same type used after the basifying step (cut-off: 0.8 μm). The retentate contained the granules of purified PHA, whereas the permeate was used for the aforementioned dilution steps.

The retentate was subjected to a further filtration operation through a candle filter, in which the suspension was introduced with a pressure equal to 4.0 bar, from which an aqueous permeate and a concentrated suspension were obtained, the latter being then subjected to drying by a fluid bed dryer at 180° C., so as to obtain a powder of PHA with a water content lower than 0.5% by weight.

EXAMPLE 3

The example 1 was repeated in the same conditions starting from a cell suspension of 500 L which had a dry mass concentration of 77 g/L and a PHA content equal to 53 g/L. Table 1 shows the concentrations on a dry basis of the overall mass and of the PHA measured in the various process steps, that is, after the base treatment (treated cell suspension) and at the end of the process after bleaching and tangential filtration (final PHA suspension). The PHA obtained was characterised in terms of purity, molecular weight and yield.

The molecular weight (Mw, mean ponderal molecular weight) was determined by using the device GPC-HPLC Breeze 2, Waters, provided with refractive index detectors and UV-VIS, with chromatographic column Mini Mix D (molecular weight range 200-400,000 Da). The calibration was carried out by using monodispersed polystyrene standards (Sigma Aldrich, Milano) having the following molecular weights: 2,440 Da, 13,700 Da, 29,300 Da, 50,400 Da, 105,600 Da and 370,000 Da. The flow velocity of the mobile phase was of 0.3 ml/min, whereas the concentration of the injected PHA chloroform solutions was of about 3 mg/ml.

The purity of PHA was determined by an apparatus HPLC Shimadzu with chromatographic column Alltech OA-1000. The flow velocity was of 0.7 ml/min and the mobile phase was an aqueous solution brought to pH equal to 2 with sulphuric acid. Before analysis, the PHA suspension was dried so as to obtain a powder and then the PHA was depolymerised by a methanolysis process in methanol and sulphuric acid at 3%, obtaining a degradation of the polymer in its monomers.

TABLE 1

| Step | Volume (L) | Dry mass concentration (g/L) | Concentration PHA (g/L) | Purity (%) | Yield (%) | Mw (kDa) |
|---|---|---|---|---|---|---|
| Initial cell suspension | 500 | 77.0 | 53.0 | — | 100 | 320 |
| Treated cell suspension | 372 | 65.0 | 59.1 | — | 83 | 297 |
| PHA final suspension | 285 | 73.2 | 72.5 | 99 | 78 | 278 |

The data shown in Table 1 highlight that the PHA obtained had a purity of 99%, a yield of 78% and a molecular weight 278 kDa. The shown data are the result of experiments carried out on 20 samples, thus demonstrating that they are repeatable data.

EXAMPLE 4 (COMPARISON)

Starting from the same cell suspension used in example 3, the recovery and purification process described in WO2011/045625, pages 6-8, was repeated. The PHA thus obtained was characterised as described in example 3. The data shown in Table 2 highlight that the obtained PHA had a purity of 95%, a yield of 59% and a molecular weight of 167 kDa. Also in this case, the data shown are the result of experiments carried out on 20 samples.

From the comparison of the results obtained in example 3 and 4, it is evident how, by starting from the same cell suspension containing PHA, the method of the invention allows to obtain PHA with a greater degree of purity, a greater yield and a higher molecular weight.

TABLE 2

| Step | Volume (L) | Dry mass concentration (g/L) | Concentration PHA (g/L) | Purity (%) | Yield (%) | Mw (kDa) |
|---|---|---|---|---|---|---|
| Initial cell suspension | 500 | 77.0 | 53.0 | — | 100 | 320 |
| Treated cell suspension | 387 | 52.9 | 46.6 | — | 68 | 187 |
| PHA final suspension | 300 | 54.7 | 52.1 | 95 | 59 | 167 |

The invention claimed is:

1. A process for recovering and purifying polyhydroxyalkanoates (PHA) from a cell culture, the process comprising:
   (a) acidifying the cell culture by adding an aqueous solution of an inorganic or organic acid selected from: sulfuric acid, hydrochloric acid, phosphoric acid, nitric acid, acetic acid, citric acid, or mixtures thereof, so as to obtain a pH value less than or equal to 6, and submitting the cell culture to a cell fractionation treatment using high-pressure homogenization at a temperature greater than or equal to 10° C. and less than or equal to 80° C., so as to obtain a PHA suspension;
   (b) basifying the PHA suspension thus obtained so as to obtain a pH value greater than or equal to 8;
   (c) diluting the PHA suspension and submitting the diluted PHA suspension to first tangential filtration so as to obtain a concentrated PHA suspension as first retentate and a first aqueous phase as first permeate;
   (d) submitting the concentrated PHA suspension to bleaching;

(e) diluting the PHA suspension after the bleaching and submitting the diluted bleached suspension to second tangential filtration so as to obtain a concentrated bleached PHA suspension as second retentate and a second aqueous phase as second permeate; and (f) submitting the concentrated bleached PHA suspension to drying.

2. The process of claim 1, wherein the cell culture is submitted to a preliminary step of concentration.

3. The process of claim 2, wherein the preliminary step of concentration yields a cell concentration greater than or equal to 20 grams/liter (g/L) and less than or equal to 800 g/L.

4. The process of claim 1, wherein in step (a), the cell culture is acidified so as to obtain a pH value less than or equal to 5.

5. The process of claim 1, wherein a pressure greater than or equal to 500 bar and less than or equal to 2,000 bar is applied during the homogenization.

6. The process of claim 1, wherein in step (b), the PHA suspension is basified so as to obtain a pH value greater than or equal to 9.

7. The process of claim 1, wherein the PHA suspension thus basified is treated with at least one surfactant at a temperature greater than or equal to 10° C. and less than or equal to 80° C.

8. The process of claim 1, wherein after the treatment according to step (b), the PHA suspension is diluted so as to obtain a solid concentration greater than or equal to 10 grams/liter (g/L) and less than or equal to 500 g/L.

9. The process of claim 1, wherein in at least one of the tangential filtration steps, at least one ceramic or polymeric membrane is used, having a mean pore dimension greater than or equal to 0.05 microns (μm) and less than or equal to 10 μm.

10. The process of claim 1, wherein in at least one of the tangential filtration steps, the PHA suspension is fed through at least one tangential flow filter with a pressure greater than or equal to 1 bar and less than or equal to 10 bar.

11. The process of claim 1, wherein in at least one of the tangential filtration steps, flow speed greater than or equal to 2 m/sec and less than or equal to 10 meters/second is maintained through at least one tangential flow filter.

12. The process of claim 1, wherein the bleaching step (d) is carried out by adding oxidizing agent.

13. The process of claim 1, wherein the bleaching step (d) is carried out at a temperature greater than or equal to 10° C. and less than or equal to 60° C.

14. The process of claim 1, wherein after the treatment according to step (d), the bleached PHA suspension is diluted so as to obtain a solid concentration greater than or equal to 10 grams/liter (g/L) and less than or equal to 100 g/L.

15. The process of claim 1, wherein the concentrated bleached PHA suspension obtained from step (e) is further concentrated using orthogonal filtration and then directed to the drying step (f).

16. The process of claim 15, wherein at least one flocculating agent is added to the concentrated bleached PHA suspension, and a resulting combination is then fed to the orthogonal filtration step.

17. The process of claim 1, wherein a pressure greater than or equal to 500 bar and less than or equal to 1.500 bar is applied during the homogenization.

18. The process of claim 1, wherein the PHA suspension thus basified is treated with at least one surfactant at a temperature greater than or equal to 20° C. and less than or equal to 50° C.

19. The process of claim 1, wherein after the treatment according to step (b), the PHA suspension is diluted so as to obtain a solid concentration greater than or equal to 25 grams/liter (g/L) and less than or equal to 100 g/L.

20. The process of claim 1, wherein in at least one of the tangential filtration steps, at least one ceramic or polymeric membrane is used, having a mean pore dimension greater than or equal to 0.2 microns (μm) and less than or equal to 5 μm.

* * * * *